United States Patent
LaFargue

(10) Patent No.: US 8,272,162 B2
(45) Date of Patent: Sep. 25, 2012

(54) METHOD FOR PREPARING RAW POLLEN

(75) Inventor: Marianne LaFargue, Paris (FR)

(73) Assignee: Stallergenes S.A., Antony Cedex (FR)

( * ) Notice: Subject to any disclaimer, the term of this patent is extended or adjusted under 35 U.S.C. 154(b) by 40 days.

(21) Appl. No.: 12/847,491

(22) Filed: Jul. 30, 2010

(65) Prior Publication Data

US 2011/0059528 A1    Mar. 10, 2011

Related U.S. Application Data

(60) Provisional application No. 61/231,489, filed on Aug. 5, 2009.

(30) Foreign Application Priority Data

Jul. 31, 2009  (FR) ...................................... 09 55408

(51) Int. Cl.
  *A01B 79/00* (2006.01)
  *A01B 79/02* (2006.01)
  *A01C 1/00* (2006.01)
  *A01G 1/00* (2006.01)
  *A01H 3/00* (2006.01)

(52) U.S. Cl. ..................................... 47/58.1 R; 435/410

(58) Field of Classification Search .................. 435/410, 435/69.1, 91.1, 468; 47/58.1 R
See application file for complete search history.

(56) References Cited

U.S. PATENT DOCUMENTS

| | | | |
|---|---|---|---|
| 1,969,104 A | 8/1934 | Sibley et al. | |
| 2,046,932 A | 7/1936 | Wyatt et al. | |
| 2,471,326 A | 5/1949 | Hoyt, Sr. | |
| 2,593,625 A | 4/1952 | Stokes | |
| 2,721,655 A | 10/1955 | Pritchett | |
| 2,827,749 A | 3/1958 | Patten | |
| 3,686,889 A | 8/1972 | Harza | |
| 3,986,463 A | 10/1976 | Houston et al. | |
| 4,922,651 A | 5/1990 | Atkinson et al. | |
| 5,694,700 A | 12/1997 | Greaves et al. | |
| 6,121,014 A * | 9/2000 | Koziel et al. | 435/69.1 |
| 6,982,326 B1 | 1/2006 | Griffith et al. | |
| 7,181,896 B2 | 2/2007 | Lukac et al. | |
| 7,402,667 B2 | 7/2008 | Cook et al. | |
| 2006/0053686 A1 | 3/2006 | Halwas | |

FOREIGN PATENT DOCUMENTS

| | | |
|---|---|---|
| DE | 34 07517 | 1/1986 |
| FR | 1.388.298 | 2/1965 |
| FR | 2 881 649 | 8/2006 |

OTHER PUBLICATIONS

Preliminary Search Report issued Mar. 11, 2010 for French Application No. 0955408, National Institute of Industrial Property (INPI), Paris, Cedex, France.

(Continued)

*Primary Examiner* — Kent L Bell

(74) *Attorney, Agent, or Firm* — Stites & Harbison PLLC; Marvin Petry

(57) ABSTRACT

The present invention relates to a method for preparing raw pollen which is suitable for being used for the preparation of allergen extracts. The method involves instantaneously freezing the pollen immediately after harvesting, optionally followed by drying the frozen pollen by sublimation.

20 Claims, 4 Drawing Sheets

OTHER PUBLICATIONS

Written Opinion issued Jul. 31, 2009 for French Application No. 0955408, National Institute of Industrial Property (INPI), Paris, Cedex, France, with computer generated English translation of Point V thereof.

Preliminary Search Report issued Mar. 4, 2010 for FR 0955410, National Institute of Industrial Property (INPI), Paris, Cedex, France.

Preliminary French Search Report issued Mar. 4, 2010 for FR 0955411, National Institute of Industrial Property (INPI), Paris, Cedex, France.

Written Opinion issued Jul. 31, 2009 for FR 0955411, National Institute of Industrial Property (INPI), Paris, Cedex, France, with Computer generated English translation of Point V thereof.

* cited by examiner

METHOD FOR PREPARING RAW POLLEN

CROSS REFERENCE TO RELATED APPLICATIONS

This application claims benefit of U.S. Provisional Application No. 61/231,489, filed Aug. 5, 2009 (which is hereby incorporated by reference).

The present invention relates to a method for preparing raw pollen which is suitable for being used for the preparation of allergen extracts. The method involves instantaneously freezing the pollen immediately after harvesting, optionally followed by drying the frozen pollen by sublimation.

Harvesting pollen, in particular grass, herbaceous plant or tree pollen, is generally carried out using pollen harvesting machines which operate in fields during the months at the end of spring and summer, at temperatures which are often high.

The harvesting machines which are generally used comprise a motorised chassis on which various means are mounted, including means which are in the form of a head for harvesting pollen by means of suction and which are connected, via means in the form of a separation cyclone, to means which form a suction fan. These various means are connected by an assembly of ventilation ducts and the means in the form of a separation cyclone are associated with means in the form of a pollen recovery hopper.

A harvesting machine of this type may comprise two suction circuits in parallel, each comprising means in the form of a suction fan and means in the form of a separation cyclone, these being connected by means of ducts and connectors to pollen harvesting heads which are arranged in the form of a ramp placed at the front of the machine.

This ramp is carried, for example, by a fork which is adjustable in terms of height to adapt to the height of the species to be harvested and whose angle relative to the ground can also be adjusted. This ramp can be produced in conventional manner in the form of a plurality of portions which can be folded in order to allow this machine to travel on roads.

These means both allow the pollen to be separated from the plants and allow it to be recovered therefrom by means of suction.

However, the use of such a machine has revealed a given number of problems.

Problems have occurred with agglomeration of the harvested pollen and fermentation thereof.

The harvesting of pollen is mainly carried out under high temperature conditions. Nonetheless, the collected pollen is very damp and exposure to these high temperatures during the harvesting time leads to an agglomeration of pollen which makes the recovery of the pollen extremely difficult. With the pollen collection methods used with existing machines, it is estimated that the pollen which is then processed for the extraction of allergens represents approximately only 5% of the total volume collected.

In addition to this problem of agglomeration, there is a problem concerning fermentation which is also linked to the high temperatures at the time of harvesting, which results in a reduction in the allergenic activity of the collected pollen and an undesirable increase of the microbiological flora (bacteria, yeasts, moulds) in the collected product. Since the pollen is used for the extraction of allergens which are then intended for the preparation of anti-allergy medication or diagnostic tests, the microbiological load of the product must remain lower than the maximum load defined by the European Pharmacopoeia.

The object of the invention is therefore to provide a method for preparing raw pollen which prevents these problems of agglomeration and fermentation of harvested pollen.

To this end, the invention relates to a method for preparing raw pollen which involves flash freezing of the pollen at the time at which it is harvested, before the pollen begins to agglomerate. The collected pollen, which is immediately subjected to a flash freezing operation, is in the form of a frozen powder which can then be dried, preferably by means of lyophilisation, in order to provide a raw pollen which is suitable for being used for the preparation of allergen extracts.

In this manner, the method for preparing raw pollen according to the invention comprises the steps of:

a) harvesting the pollen;
b) subjecting the harvested pollen to a flash freezing operation in a period of time following its harvesting such that the pollen does not begin to agglomerate. This method allows a frozen pollen powder to be obtained.

The period of time such that the pollen does not begin to agglomerate, after harvesting of the pollen, depends on the temperature and humidity conditions at the time at which the pollen is harvested. A sufficient period of time can be readily determined by the person skilled in the art, for example, by observing the state of the harvested pollen. Typically, the harvested pollen can be subjected to a flash freezing operation, for example, within 10 minutes, preferably 5 minutes, even more preferably 2 minutes of the harvesting of the pollen. As will be apparent to the person skilled in the art, this period of time must preferably be complied with for each of the grains of pollen. In this manner, each grain of harvested pollen can be subjected to a flash freezing operation, for example, within 10 minutes, preferably 5 minutes, even more preferably 2 minutes of the harvesting of this grain of pollen.

In practice, since the pollen is most generally harvested in a continuous manner for one or more hours with a harvesting machine, it cannot be envisaged to wait until the end of the harvest to subject the pollen to a flash freezing operation, unless the harvest is interrupted regularly to remove the harvested pollen and subject it to a flash freezing operation without waiting for the end of the harvest.

Therefore, the method for preparing raw pollen according to the invention preferably comprises the steps of:

a) harvesting a grain of pollen; and
b) subjecting the harvested grain of pollen to a flash freezing operation in a period of time following its harvesting such that the grain does not begin to agglomerate with other harvested grains of pollen in order to obtain a frozen pollen powder,
c) repeating steps a) and b) as many times as necessary.

This embodiment also relates to a method for preparing raw pollen according to the invention which preferably comprises the steps of:

a) harvesting the pollen;
b) immediately subjecting the harvested pollen to a flash freezing operation. This method allows a frozen pollen powder to be obtained.

For the flash freezing operation, the harvested pollen is exposed to a temperature less than or equal to −20° C., for example, less than or equal to −25° C., less than or equal to −30° C., or less than or equal to −50° C. However, the temperature may remain greater than −80° C., for example. The fresh grain of pollen has a significant content of water (approximately 40%) and exposure to a temperature less than or equal to −20° C. leads to flash freezing of the water of the grains of pollen, thus forming a frozen powder. The flash freezing of the pollen thus prevents the problems of agglomeration of the pollen linked to the combination of the high degree of moisture in the collected pollen and the high temperature conditions under which the harvesting of the pollen is generally carried out.

Furthermore, the microbiological development within the product is blocked by the freezing of the harvested pollen.

It has also been found that the allergenic activity of the collected pollen which is instantaneously frozen is greater than that of a pollen collected without freezing.

Without wishing to be bound by a hypothesis, the freezing could limit the degradation of the allergens in the pollen owing to the exposure to heat or the water in the collected product could extract the allergens from the pollen, the transfer of the allergens to the water being blocked by the freezing.

The flash freezing can be carried out using a freezing means such as dry ice or liquid nitrogen, or any other appropriate means, by placing the harvested pollen directly in contact with the freezing means, or by placing the harvested pollen indirectly in contact with the freezing means, for example, by recovering the pollen in a receptacle which is associated with freezing means and around which thermal insulation is arranged.

The most satisfactory method for harvesting and instantaneously freezing the pollen, in particular immediately after harvesting, is to use a pollen harvesting machine of the type comprising a motorised chassis on which there are mounted means which are in the form of a head for harvesting pollen by means of suction and which are connected, via means in the form of a separation cyclone, to means forming a suction fan, the means in the form of a cyclone being associated with means in the form of a pollen recovery hopper, characterised in that it comprises means for freezing the pollen harvested in the means in the form of a recovery hopper.

The pollen harvesting machine comprises one or more of the following features:
- the means in the form of a recovery hopper comprise an actual hopper around which thermal insulation is arranged,
- the means in the form of a hopper comprise a flap for introducing dry ice therein,
- the means in the form of a hopper comprise means for introducing liquid nitrogen therein,
- the base of the means in the form of a pollen recovery hopper comprises a flap for emptying and collecting the frozen pollen,
- the means in the form of a pollen harvesting head comprise an assembly of suction hoods, each of which has a first portion generally of frustoconical form, which widens between an opening for connection to the remainder of the circuits of the machine and a polygonal base,
- the polygonal base is square,
- the suction hoods are arranged in the form of a suction ramp which is carried by a fork which can be adjusted in terms of position, height and inclination, and which is fixed to the front of the machine, and
- it comprises two parallel suction circuits, one of which is connected to the hoods of the left-hand portion and the other of which is connected to the hoods of the right-hand portion of the suction ramp, these circuits each comprising means in the form of a separation cyclone, means forming a suction fan and means in the form of a pollen recovery hopper.

The machine will be better understood from a reading of the following description, given purely by way of example and with reference to the appended drawings, in which:

FIG. 1 illustrates a pollen harvesting machine which is designated 1.

This machine comprises, for example, a motorised chassis of an appropriate type, at the front of which there is arranged a fork 2 for supporting a ramp 3 of heads for harvesting pollen by means of suction.

These heads will be described in greater detail below and the ramp can be adjusted in terms of position, that is to say, in terms of height and inclination.

Figure 1:
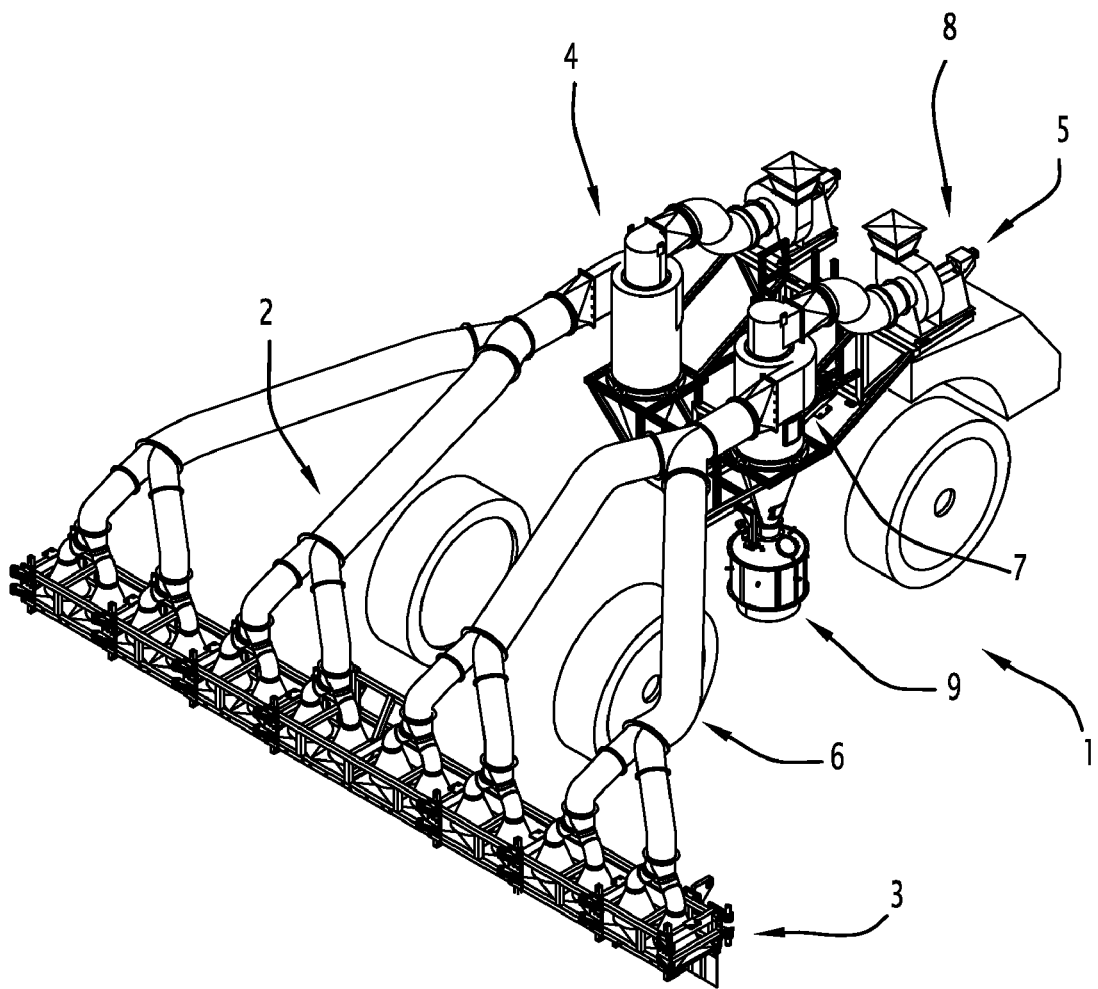
FIG. 1 is a schematic diagram illustrating the structure of a machine according to the invention.

The corresponding heads of the ramp placed at the left and right thereof are connected to parallel suction circuits and are designated 4 and 5, in this FIG. 1, respectively.

Each circuit such as, for example, the circuit 5 comprises an assembly of connection ducts, such as, for example, a duct which is designated 6, which allows the corresponding suction heads to be connected to corresponding means in the form of a separation cyclone designated 7.

These means 7 in the form of a separation cyclone are placed in the intermediate portion of the machine and are themselves connected by means of ducts to means in the form of a suction fan which are designated 8 and which are placed at the rear of the machine.

By way of example, these means in the form of a fan may have an output of 6000 $m^3$/hour for a rotation speed, for example, of 2400 rpm. Each ventilation means controls the suction over one half of the ramp 3 of suction heads.

The motors of the ventilation means may, for example, be formed by hydraulic motors which are supplied with electrical power from a source of energy which is provided on the chassis. The suction speeds may also be adjustable from a cabin of the chassis independently for each fan.

It is possible to use an electrically controlled proportional valve to adjust the hydraulic flow in the motors and therefore to control the rotation speed thereof.

The flow of drawn-in air thus generated is transferred from the ramp of suction heads to the fans by an assembly of flexible ventilation ducts. This assembly of ducts is optimised in order to prevent pollen from being deposited on the walls. The lengths of the ducts are optimised and the potential retention zones minimised.

This assembly can be completely disassembled and cleaned in order to allow, for example, ducts to be changed between each species of pollen harvested.

Such an assembly allows an air intake speed of greater than 15 m/second, for example, to be achieved in the region of the top of each suction head.

The means 7 in the form of a separation cyclone themselves allow the drawn-in particles to be separated, that is to say, the pollen plus various debris, from the flow of drawn-in air. These particles are then recovered in means in the form of a recovery hopper which are associated with these means in the form of a cyclone.

One of these means in the form of a recovery hopper is designated 9 in FIG. 1. The dimensions of the means in the form of a cyclone are optimised in order to allow a separation of the pollens from the flow of air of close to 100%.

After separation, the pollen falls into the means in the form of a recovery hopper which, in the example illustrated, are placed under each means in the form of a cyclone at each side of the chassis of the machine.

In the illustrated embodiment, the suction ramp 3 comprises eight suction heads which are connected by means of corresponding ducts and connectors to one of the suction circuits described above.

Figure 2:
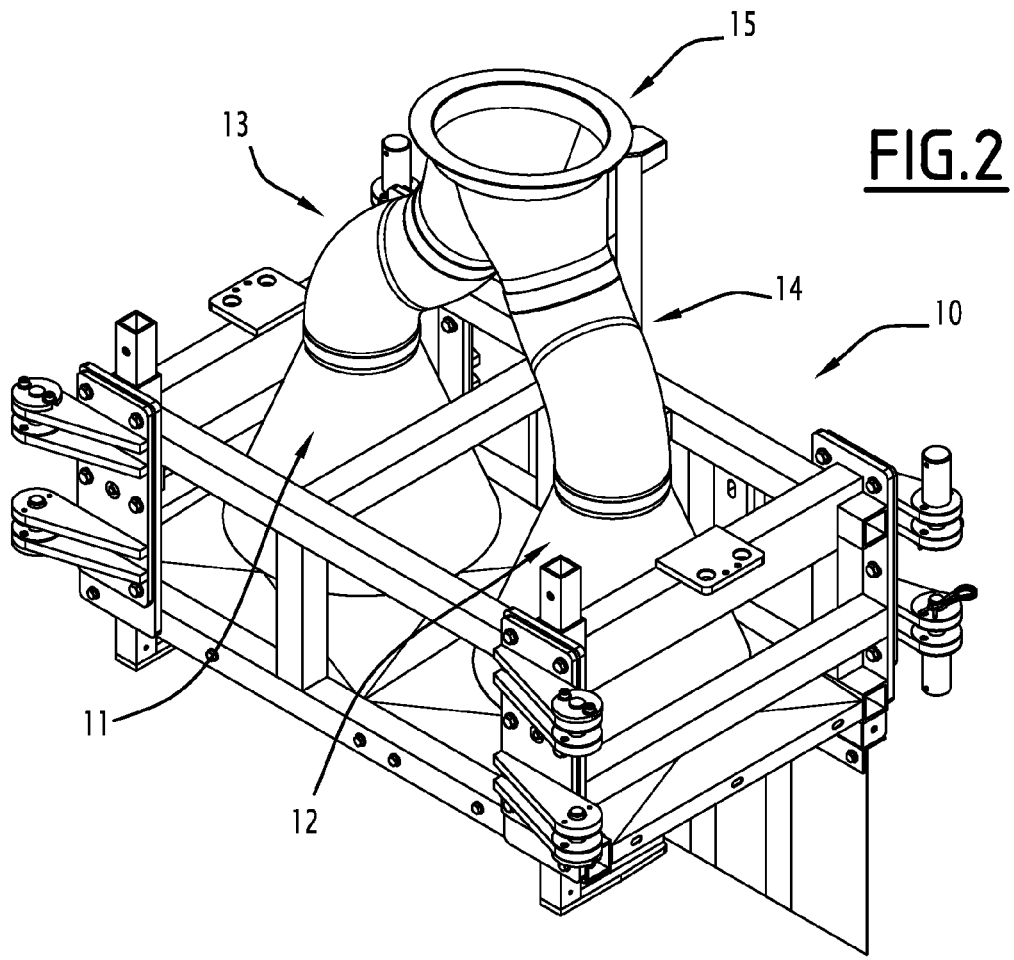
FIG. 2 illustrates a suction head involved in the constitution of such a machine.

One of these suction heads is illustrated in greater detail in FIG. 2.

This head is designated 10 and comprises in the illustrated example two suction hoods 11 and 12, respectively, which are associated with each other and positioned side by side.

Each hood has an open end which is connected via a respective duct 13 and 14 to a connector 15, the connector itself being branched off from one of the suction circuits described above, such as the circuit 5.

The configuration of the hoods has been optimised with respect to ventilation in order to allow a minimal suction speed over the largest possible surface-area thereof.

Figure 3:
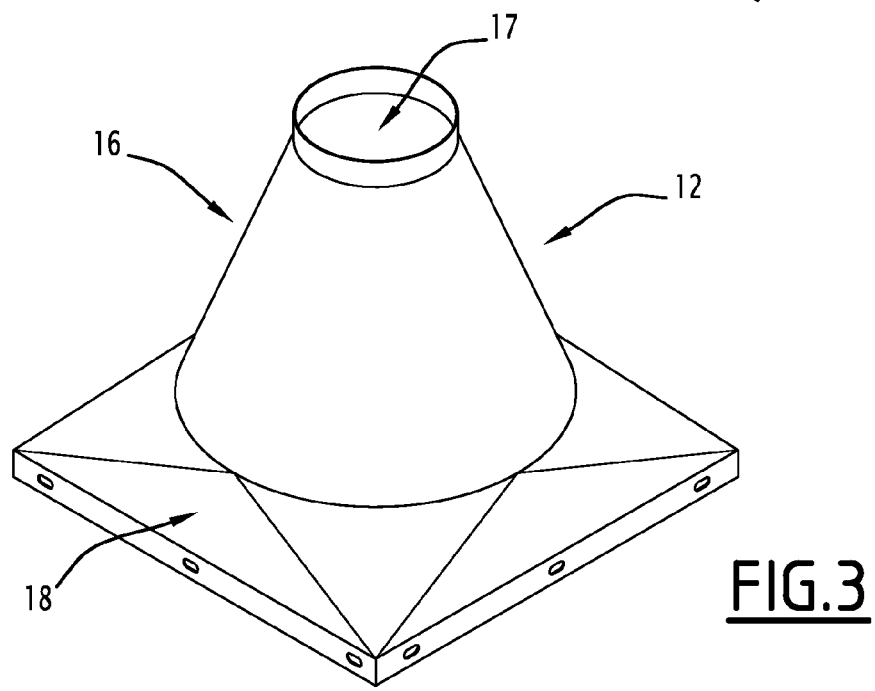
FIG. 3 illustrates a suction hood involved in the constitution of such a head.

Such a hood is illustrated in greater detail in FIG. 3.

This hood is, for example, the hood designated 12 and it comprises a frustoconical portion which is designated 16 and which extends so as to widen between an opening 17 for connection, for example, to the duct 14 and a polygonal base 18, which is, for example, square.

With the values mentioned above and such a shape, a suction speed greater than 1 m/second over more than 75% of the surface-area of the hood, and in particular of the base thereof, is obtained.

This hood noticeably improves the efficiency of the suction compared with the suction means which exist in the prior art.

Furthermore, and in order to further improve the efficiency of these suction heads, means, such as, for example, cables, can be placed in a horizontal manner in front of the hoods, these means being adjustable in terms of position in order to shake the plants when the machine passes, in order to further optimise the release of pollens by the plants.

Figure 4:
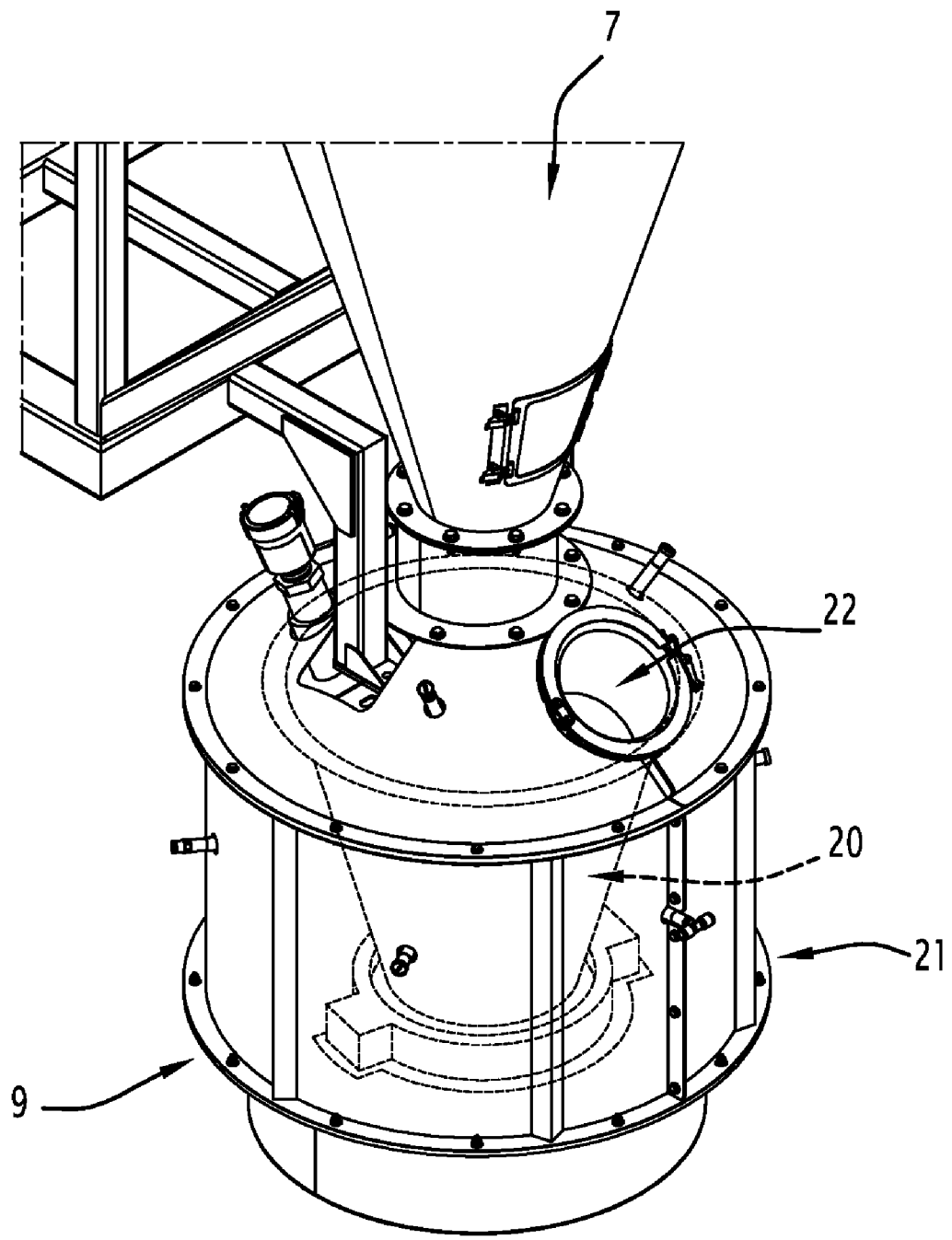
FIG. 4 illustrates the means in the form of a pollen recovery hopper involved in the constitution of such a machine.

FIG. 4 illustrates an embodiment of means in the form of a pollen recovery hopper.

As indicated above, pollen recovery means, such as, for example, the means designated 9, are placed below the corresponding means in the form of a cyclone, such as, for example, the means 7.

In the machine according to the invention, these pollen recovery means comprise an actual hopper which is designated 20 and around which there is placed thermal insulation which is designated 21.

At the upper end thereof, this hopper 20 is connected to the cyclone 7 and comprises, for example, a flap 22 which allows dry ice to be introduced into the hopper in order to bring about flash freezing of the harvested pollen.

The inner side of the hopper is preferably kept at a temperature less than or equal to −20° C., for example, less than or equal to −25° C., less than or equal to −30° C., or less than or equal to −50° C. However, the temperature may remain higher than −80° C., for example.

The introduction of this dry ice into the hopper can be carried out, for example, by an operator.

Of course, it is self-evident that other embodiments of these means for freezing pollen can be envisaged.

In this manner, for example, means for introducing liquid nitrogen may also be provided.

Other means can also be envisaged.

It should also be noted that the base of the hopper 20 can be provided with means for recovering the pollen frozen in this manner.

Various embodiments of these means may be envisaged, such as, for example, cartridge-type means, drawer-type means, etc.

It should also be noted that the recovery hopper 20 may, for example, be provided with means which form a temperature sensor and means which form a level detector, whose output information is transmitted, for example, into the cabin of the machine in order, for example, to allow an operator to verify that the pollen harvested really is frozen and that the hopper is not full, in order to take corrective action as necessary, such as, for example, adding dry ice or emptying the hoppers in order to recover the pollen.

It has been found that the operation for freezing pollen harvested in the harvesting machine described above allowed the problems set out above of agglomeration and fermentation of the pollen to be solved.

Figure 5:
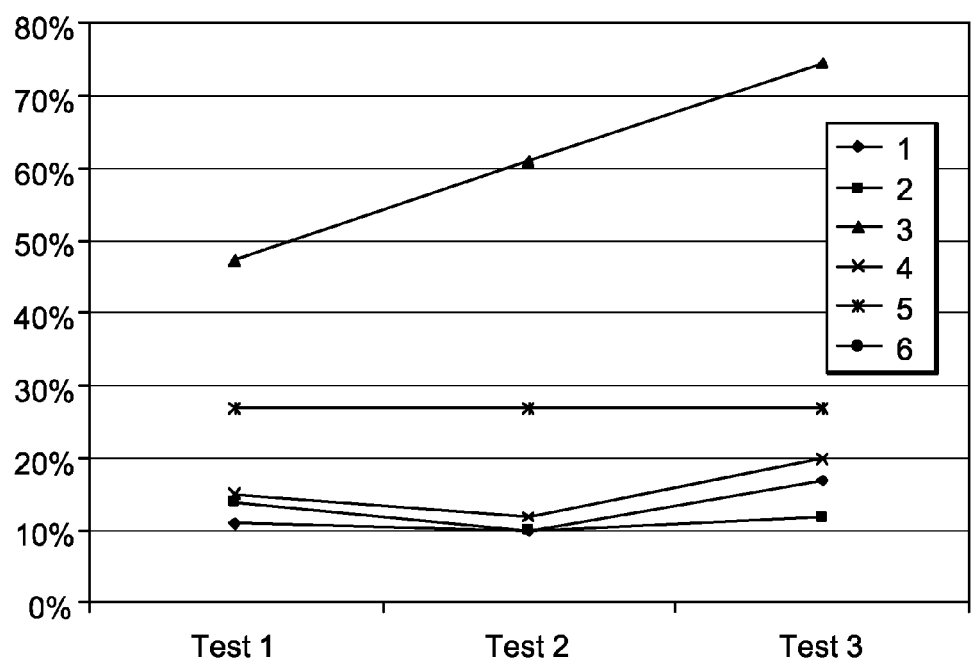
FIG. 5 is a graph showing tests using different techniques for drying pollen and the results.

In the hopper, the pollen is in the form of a frozen powder, which remains in this form for the entire duration of the harvest. After the harvest is complete, the frozen pollen can then be recovered without having been subject to any alteration. In this manner, with the harvesting machine described above, the quantity of pollen which can then be used for the extraction of allergens consequently represents up to 75% or 85% of the total volume of collected pollen (see FIG. 5).

The collected pollen may be grass pollen, herbaceous plant pollen, but also tree pollen, such as the pollens of cocksfoot, meadow cat's tail grass, vernal grass, rye grass, meadow grass, ambrosia, artemisia, pellitory-of-the-wall, plantain, ash, olive, oak, plane, birch, cypress, juniper, thuja, cedar.

According to one embodiment of the method for preparing raw pollen according to the invention, the frozen pollen is then dried by sublimation in order to provide dried raw pollen.

The invention thus relates to a method for preparing raw pollen which comprises the steps of:
a) harvesting the pollen;
b) immediately subjecting the harvested pollen to a flash freezing operation; and
c) drying the frozen pollen of step b) by sublimation until the pollen has a water activity of less than 0.35 Aw.

The water activity represents the water vapour pressure of a wet product over the saturating vapour pressure at the same temperature.

The water activity is measured by a (graduated) device for measuring the water activity.

Several techniques and devices for drying frozen pollen have been tested: ovens, vacuum ovens, and a lyophiliser. It has been found that drying in an oven, even under reduced pressure, does not allow the water to be discharged in an adequate manner and the defrosting of the pollen is accompanied by a complete agglomeration of the product. The level of collected pollen which can then be used for the extraction of allergens consequently only represents from 10 to 30% of the total volume of collected pollen.

However, the use of a lyophiliser, that is to say, drying by sublimation, allows up to 75% or 85% of the collected pollen to be recovered.

The inventors have dried pollen in accordance with different techniques and have compared the yields of finished pollen obtained. The results obtained are set out in FIG. 5 for three independent tests. This figure represents the percentage of pollen having a size of less than 56 μm that is recovered after sieving under suction, compared with the total pollen present in the sample. The drying systems which have been used are the following:
line 1: Eratis® oven with plate system
line 2: Eratis® oven with Osmofilm® system
line 3: lyophiliser line 4: dryer
line 5: vacuum oven with plate system
line 6: vacuum oven with Osmofilm® system It should be noted that, owing to lyophilisation, the yield of the processing of the raw pollen into finished pollen is much better than that of a product dried in a conventional oven, or a vacuum oven. The drying by sublimation can be carried out directly on the frozen pollen, without necessarily having to lower the temperature thereof beforehand. Preferably, the drying by sublimation is carried out at the freezing temperature of the pollen, that is to say, preferably at a temperature less than or equal to −20° C., for example, less than or equal to −25° C., less than or equal to −30° C., or less than or equal to −50° C. The temperature may remain greater than −80° C., for example. However, it is possible in the context of the method according to the invention to lower the temperature of the frozen pollen, for example, by 10° C. or 20° C. or more before sublimation.

The drying by sublimation can be carried out at a pressure less than or equal to 70 Pa (700 μbar), for example, less than or equal to 50000 Pa (500 μbar), less than or equal to 30 Pa (300 μbar). Advantageously, the pressure may be between 30 Pa (300 μbar) and 60 Pa (600 μbar), preferably between 40 Pa (400 μbar) and 50 Pa (500 μbar).

The drying by sublimation can be carried out in one or more steps, each characterised by specific temperature and pressure conditions. However, drying by sublimation in a single step is sufficient.

Drying by sublimation may, for example, be carried out at a temperature of between −20° C. and −50° C., at a pressure of between 40 and 60 Pa. Preferably, the drying is carried out at a temperature of between −20° C. and −35° C. at a pressure of between 40 and 55 Pa.

The duration of the drying operation is in accordance with the degree of humidity of the pollen at the time at which it is harvested. The drying step by sublimation may typically last from 20 to 60 hours, for example, from 24 to 50 hours, or from 25 to 48 hours. The duration of the sublimation required to obtain a pollen having a water activity of less than 0.35 Aw can be determined experimentally on a sample. The duration of the sublimation cycle may then be applied to the frozen pollen to be lyophilised, verifying then that the water activity level of the dry product is in accordance with that anticipated.

Preferably, the drying is carried out up to a water activity value greater than 0.05 Aw.

The invention claimed is:

1. A method for preparing raw pollen, comprising the steps of:
    harvesting pollen with equipment which takes the pollen off of the plants while in the ground, and
    flash freezing the harvested pollen in a period of time following its harvesting such that the pollen does not begin to agglomerate, to obtain frozen pollen powder.

2. A method according to claim 1, wherein the flash freezing of the harvested pollen is carried out by exposing the pollen to a temperature less than or equal to −20° C.

3. A method according to claim 1, wherein the flash freezing of the harvested pollen is carried out using dry ice or liquid nitrogen.

4. A method according to claim 1, wherein the harvesting step comprises engaging the pollen containing plants by the use of a motorized chassis which has suction heads which communicate through suction ducts with a separation cyclone and a suction fan and which includes a recovery hopper, and wherein the step of freezing the harvested pollen takes place while the harvested pollen is in the recovery hopper.

5. A method according to claim 1, wherein the pollen is grass pollen, herbaceous plant pollen or tree pollen.

6. A method according to claim 1, further comprising the step of drying the frozen pollen by sublimation.

7. A method according to claim 6, wherein the step of drying the frozen pollen continues until the pollen has a water activity of less than 0.35 Aw.

8. A method according to claim 6, wherein the drying by sublimation is carried out at the freezing temperature of the pollen.

9. A method according to claim 6, wherein the drying by sublimation is carried out at a temperature less than or equal to −20° C.

10. A method according to claim 6, wherein the drying by sublimation is carried out at a pressure less than or equal to 70 Pa.

11. A method according to claim 6, wherein the drying by sublimation is carried out at a temperature of between −20° C. and −50° C., at a pressure of between 40 and 60 Pa.

12. A method for preparing raw pollen, comprising the steps of:
    harvesting the pollen with equipment which takes the pollen off of plants while in the ground, and
    immediately as the pollen is harvested, flash freezing the harvested pollen in order to obtain frozen pollen powder.

13. A method according to claim 12, wherein the flash freezing of the harvested pollen is carried out by exposing the pollen to a temperature less than or equal to −20° C.

14. A method according to claim 12, wherein the flash freezing of the harvested pollen is carried out using dry ice or liquid nitrogen.

15. A method according to claim 12, wherein the harvesting step comprises engaging the pollen containing plants by the use of a motorized chassis which has suction heads which communicate through suction ducts with a separation cyclone and a suction fan and which includes a recovery hopper, and wherein the step of freezing the harvested pollen takes place while the harvested pollen is in the recovery hopper.

16. A method according to claim 12, wherein the pollen is grass pollen, herbaceous plant pollen or tree pollen.

17. A method according to claim 12, further comprising the step of drying the frozen pollen by sublimation.

18. A method according to claim 17, wherein the step of drying the frozen pollen continues until the pollen has a water activity of less than 0.35 Aw.

19. A method according to claim 18, wherein the drying by sublimation is carried out at the freezing temperature of the pollen.

20. A method according to claim 18, wherein the drying by sublimation is carried out at a temperature less than or equal to −20° C.

* * * * *